(12) United States Patent
Pinsonnault et al.

(10) Patent No.: US 6,652,469 B2
(45) Date of Patent: Nov. 25, 2003

(54) MOVEMENT DETECTOR PAD WITH RESILIENT PLATE ATTACHMENT

(75) Inventors: Maurice Pinsonnault, Westmount (CA); Claude Mauffette, Montreal (CA); David Dredge, Axminster (GB)

(73) Assignee: 34160704 Canada Inc., Ile des Soeurs (CA)

( * ) Notice: Subject to any disclaimer, the term of this patent is extended or adjusted under 35 U.S.C. 154(b) by 212 days.

(21) Appl. No.: 09/887,122

(22) Filed: Jun. 25, 2001

(65) Prior Publication Data

US 2002/0198464 A1 Dec. 26, 2002

(51) Int. Cl.$^7$ .............................. A61B 5/103; A61B 5/08
(52) U.S. Cl. ............................. 600/534; 5/655; 600/529; 600/595
(58) Field of Search ..................... 5/424, 655; 600/534, 600/552, 595, 529

(56) References Cited

U.S. PATENT DOCUMENTS

| | | | | |
|---|---|---|---|---|
| 4,657,026 A | * | 4/1987 | Tagg ........................... | 600/534 |
| 4,782,541 A | * | 11/1988 | Tuchman ...................... | 5/424 |
| 5,235,989 A | * | 8/1993 | Zomer ......................... | 600/534 |
| 5,271,412 A | * | 12/1993 | Shtalryd et al. ............ | 600/534 |
| 5,435,317 A | * | 7/1995 | McMahon et al. ........... | 600/534 |
| 6,146,332 A | * | 11/2000 | Pinsonneault et al. ...... | 600/534 |

* cited by examiner

Primary Examiner—George L. Walton
(74) Attorney, Agent, or Firm—Ogilvy Renault; Guy J. Houle

(57) ABSTRACT

Resilient attachment members interconnect a pair of flat plates of a movement detector pad and are preferably disposed in the corners of these flat plates. A piezoelectric transducer is disposed centrally between the plates to generate signals when the plates move with respect to one another. In one embodiment the resilient attachment members each have a connector pin which is connected to one of the plates and extends into a pin receiving hollow node formed in the other plates and projecting above an inner surface of the other plate. The end of the connector pin has lateral projections to engage within the node when both plates are spaced apart a predetermined distance by the pressure of helical springs which are disposed about each pin and its associated node. During movement of the pin within the node the pin is in substantially friction free movement whereby not to corrupt the movement signal generated by the piezoelectric crystal. These resilient attachment members interconnect the plates together while providing flexion thereof and which have the effect of maximizing the movement signal to the piezo by reducing the shunt effect that a more rigid corner plate connection has. The resilient members may also be constituted by leaf springs formed integral with one of the plates and connected to the other.

19 Claims, 4 Drawing Sheets

MOVEMENT DETECTOR PAD WITH RESILIENT PLATE ATTACHMENT

TECHNICAL FIELD

The present invention relates to a movement detector pad which comprises a pair of plates between which a piezoelectric compression transducer is secured and more specifically to resilient attachment members which interconnect the plates together and provide attachment and resilient displacement of the plates with respect to one another.

BACKGROUND ART

Reference is made to U.S. Pat. No. 6,146,332 which discloses a motion detector of the general type as described herein. In that patent the collector and backing plates are molded from plastic material and interconnected together by connector posts which are rigidly secured in the corner of the plates at distances which are remote from the piezoelectric compression transducer. Therefore, the plates in these corner areas are fairly rigid and will shunt any force applied to these corner areas due to its rigidity thereby often not detecting movement over these corner areas.

In that patent it is also disclosed that to maintain the plates substantially in parallel planes, due to the fact that support posts are provided in the corners only, resilient supports are provided at other locations and particularly adjacent the side edges of the plates in alignment with the central transducer. These resilient supports are helical compression springs which are retained captive within opposed recesses formed in the collector plate as well as the backing plate. These compression springs have a selected compression strength sufficient to maintain the plates spaced apart, in the area of the transducer, and permitting the plates to flex towards one another for sensing the displacement of a load positioned above a mattress or any other medium disposed on top of a detector. In particular, this movement detector is to detect child movement over a mattress of a crib. These helical compression springs do not resolve the above-mentioned problem of stiffness in the corner areas of the plates shunting movement thereover.

SUMMARY OF INVENTION

It is a feature of the present invention to provide a movement detector which substantially overcomes the above-mentioned disadvantages of the prior art.

According to the above feature, from a broad aspect, the present invention provides a movement detector comprising a pair of flat plates supported spaced apart in juxtaposed facial alignment and disposed substantially parallel relationship by resilient attachment members which are secured between the plates at predetermined positions adjacent an outer circumferential edge of the plates. A piezoelectric compression transducer is secured between the plates substantially centrally thereof and generates electric signals when the plates are displaced with respect to one another by displacement of an exterior load positioned above a top one of the plates. The top one of the plates is a collector plate and the other plate is a backing plate. The resilient attachment members spring bias the plates apart and interconnect the plates in the corner areas of the plates.

According to a further broad aspect, the attachment members each have a connector pin connected to one of the plates and extending transversely to an inner surface of one of the plates. The connector pin has lateral projecting means spaced a predetermined distance from the inner surface. A pin receiving hollow node projects above an inner surface of the other of the plates and aligned with the connector pin. The hollow node has a flat top wall with a hole therein for receiving the pin therethrough. A ledge is formed about the hole by the top wall. The pin extends into the hole with the lateral projecting means captive thereunder and disposed for facial contact with an inner face of the ledge when biased thereagainst. A helical spring is retained in position about the connector pin and the pin receiving node and between said plates to spring bias the plates apart with the plates being connected together by the connector pin captive in the node with the lateral projecting means spring biased against the ledge.

According to a still further broad aspect of the present invention the resilient attachment members are constituted by leaf springs interconnecting corner portions of the pair of plates and biasing the plates spaced apart in substantially facially aligned spaced parallel relationship.

BRIEF DESCRIPTION OF DRAWINGS

A preferred embodiments of the present invention will now be described with reference to the accompanying drawings in which.

DESCRIPTION OF PREFERRED EMBODIMENTS

Figure 1:
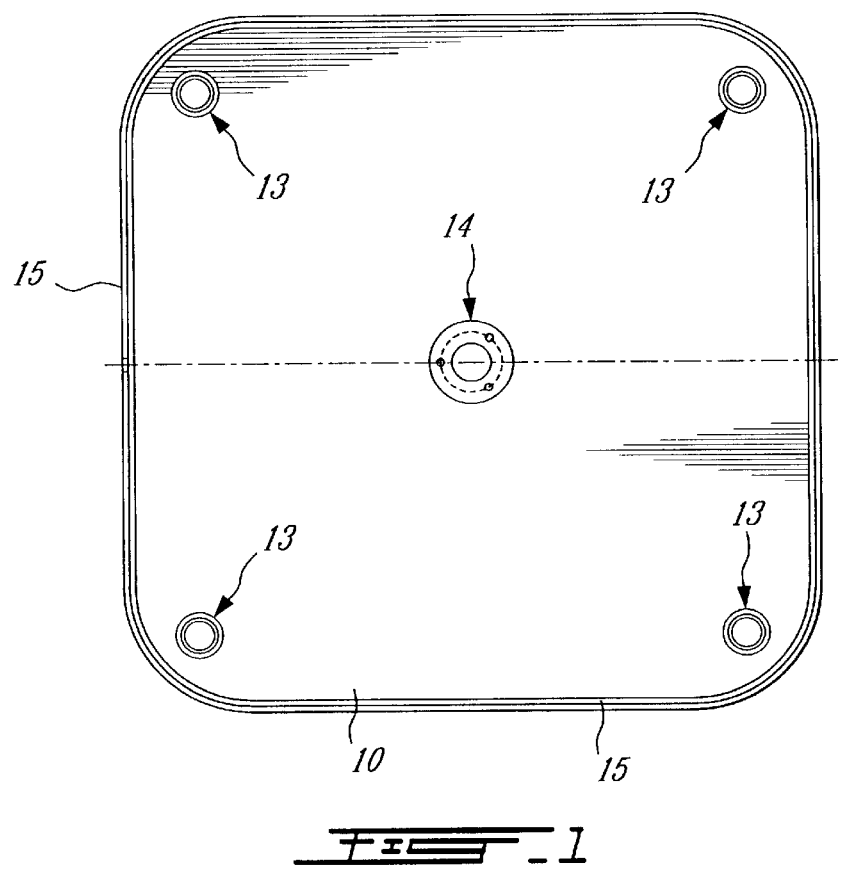
FIG. 1 is a top plan view of the inner surface of the backing plate.
Figure 5:
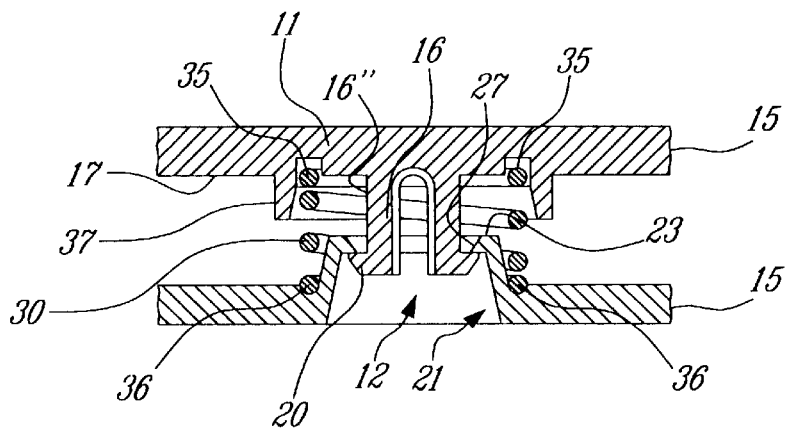
FIG. 5 is a section view showing the construction of a resilient attachment member when the plates are biased away from one another in substantially parallel relationship.
Figure 6:
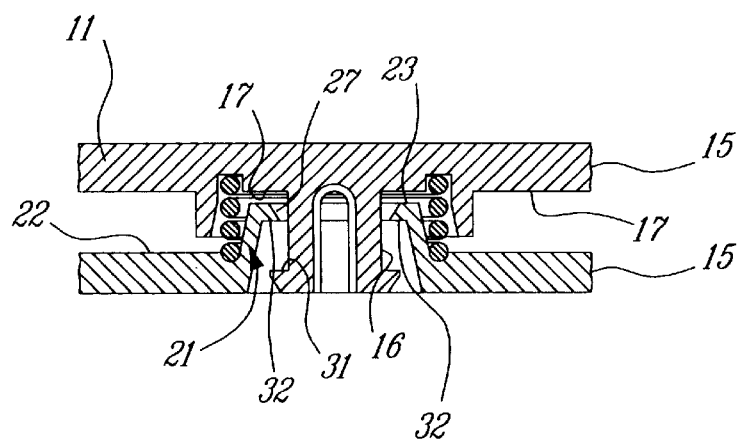
FIG. 6 is a view similar to FIG. 5 but showing the plates compressed together when a load is applied over the collector plate.
Figure 7:
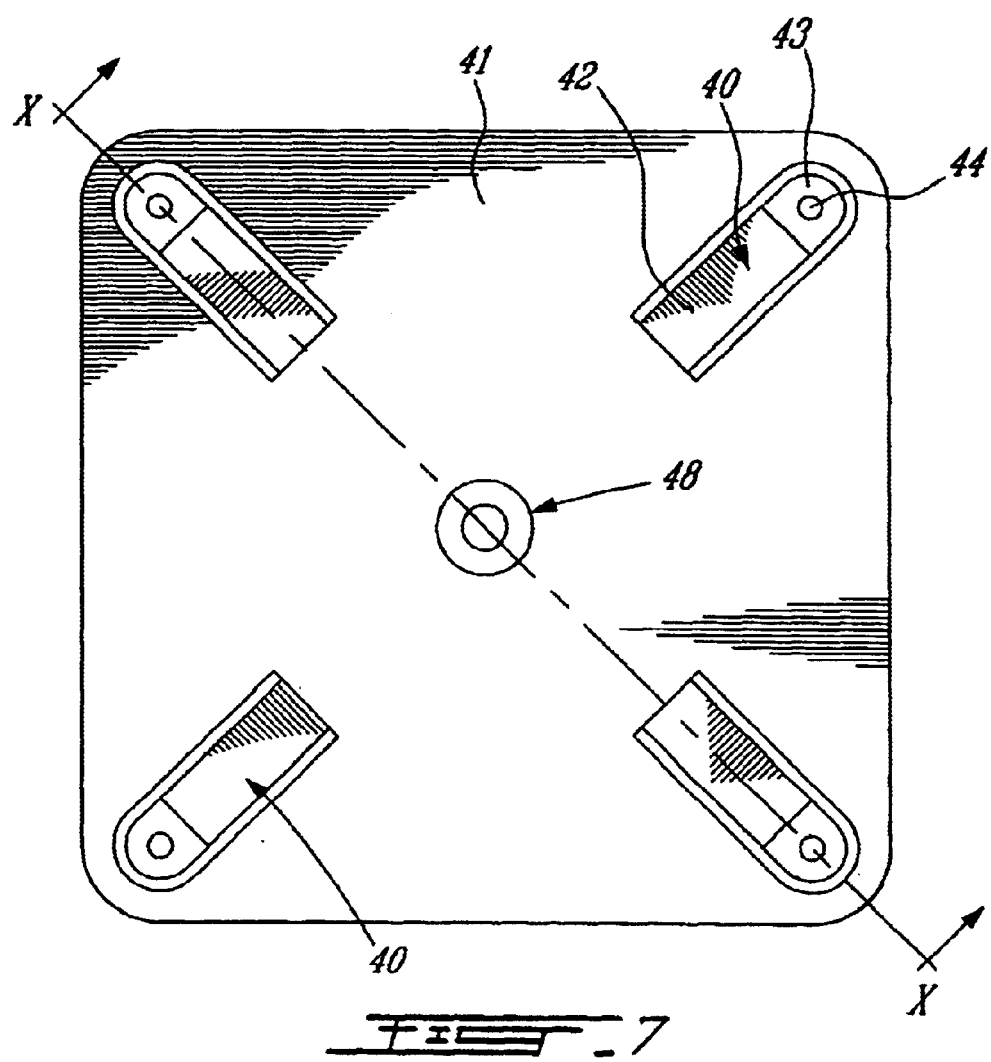
FIG. 7 is a plan view of the inner face of a base plate illustrating a further embodiment wherein leaf springs are integrally formed in the base plate.
Figure 8:
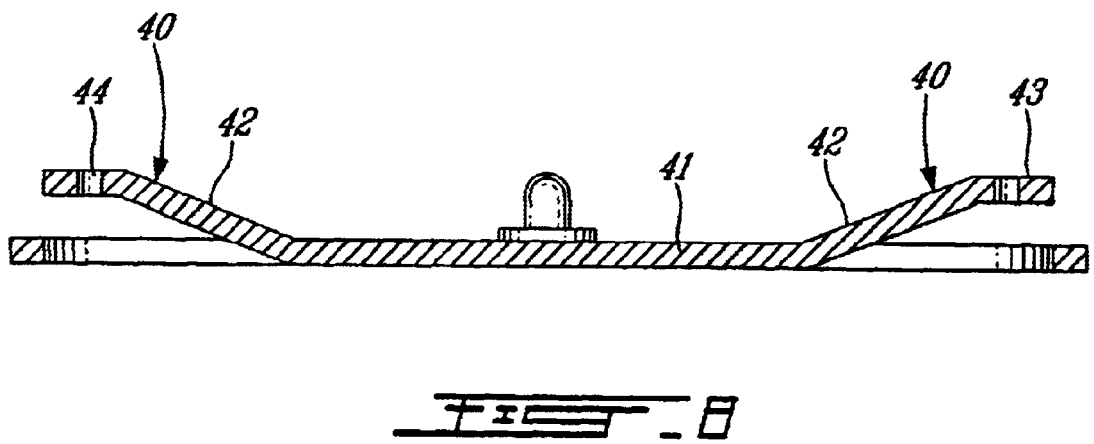
FIG. 8 is a cross-sectional side view along cross-section lines X—X of FIG. 7.
Figure 9:
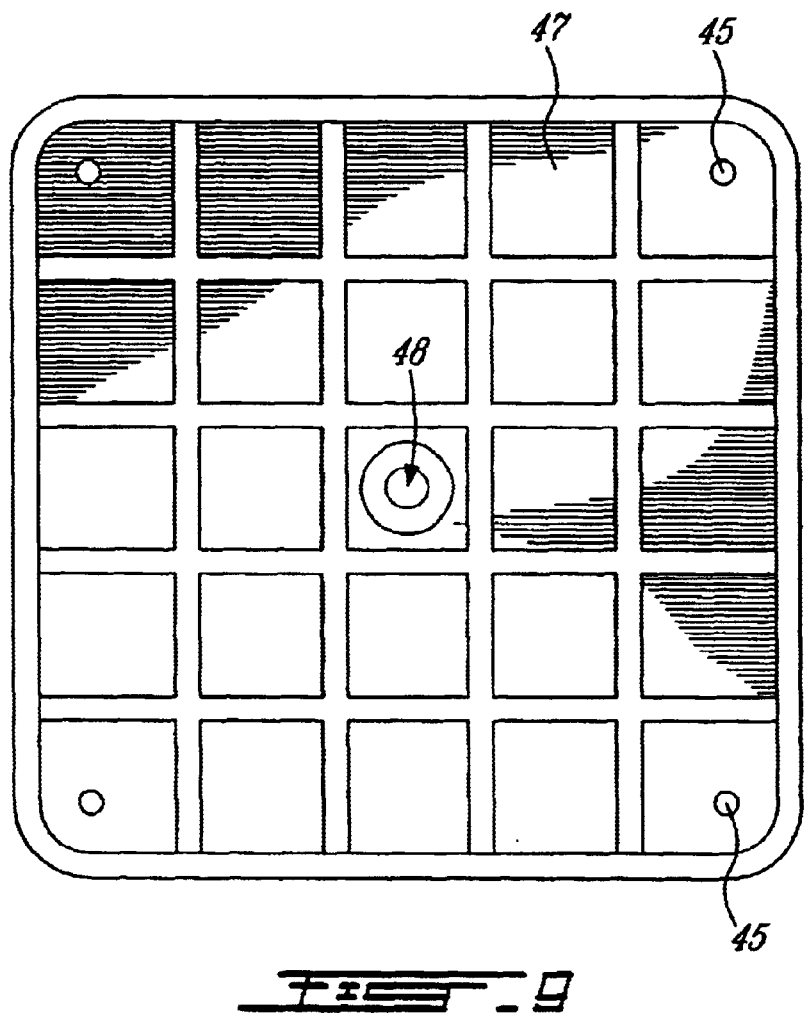
FIG. 9 is a plan view of the inner face of the collector plate associated with the base plate of FIG. 7.

Referring to the drawings and more particularly to FIG. 1, there is shown the construction of the backing plate 10 of a movement detector pad constructed in accordance with the present invention. The collector plate 11 as shown only in fragmented section in FIGS. 5 and 6 is likely shaped in contour and is attached over the backing plate 10 by resilient attachment members 12 as illustrated in assembled form in FIGS. 5 and 6. These attachment members 12 are located in the corners of the plates at the locations 13 as illustrated in FIG. 1. A piezoelectric compression transducer (not shown) is secured in the area 14 as shown in FIG. 1. The collector plate 11 and backing plate 10 are molded of rigid plastic material and they are supported spaced apart in substantially parallel relationship by the resilient attachment members 12. These attachment members 12 are preferably disposed adjacent the outer circumferential edge 15 of these plates as illustrated in FIGS. 5 and 6. A piezoelectric transducer generates electric signals when the plates are displaced with respect to one another by the displacement of an exterior load, such as an infant moving on a mattress, positioned above the collector plate. When the infant moves, the displacement is transmitted to the detector pad through the mattress.

With reference now to the additional drawings, namely FIGS. 2 to 6, the construction of the resilient attachment members 12 will now be described. Each resilient attachment member 12 is formed of a connector pin 16 connected to the collector plate 11 and extending transversely of the inner surface 17 thereof. The connecting pin 16 is a cylindrical pin having a slot 18. The pin is molded integral with the collector plate. The slot 18 sections the pin into two pin segments 16' whereby the pin segments can flex towards one another to permit ease of assembly of the pin as will be described later. The pin 16 is also provided with lateral projecting hook formations 19 extending outwardly and integrally formed adjacent the free end of each of the pin segments 16'. These hook formations also have an outwardly inclined surface 20 to provide ease of assembly.

Figure 2:
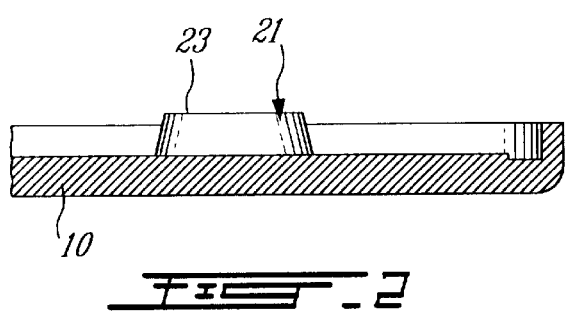
FIG. 2 is a fragmented side view, partly sectioned showing the construction of the corner of the backing plate.
Figure 3:
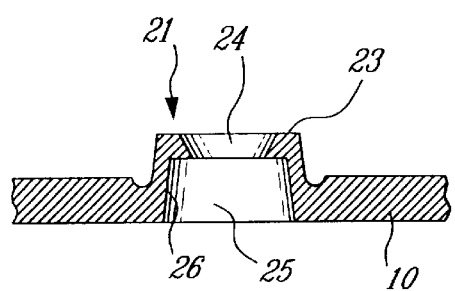
FIG. 3 is a side section view showing the construction of the pin receiving hollow node.
Figure 4:
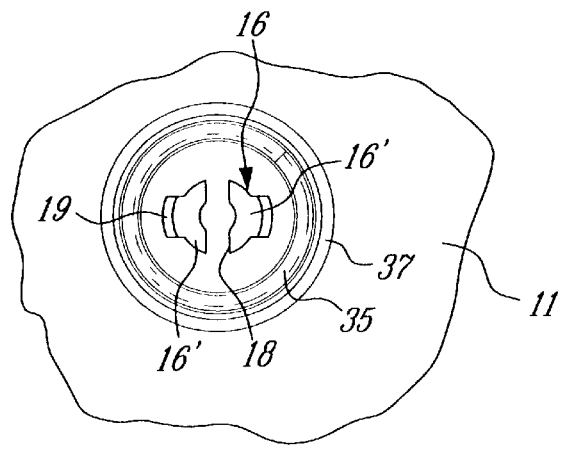
FIG. 4 is a top view showing the construction of the connector pin as seen from the inner face of the collector plate.

The resilient attachment members 12 also comprise a pin receiving node 21 which projects above the inner surface 22 of the backing plate 10 and disposed in alignment with an associated connector pin 16. The hollow node has a flat top wall 23 with a hole 24 therein and which is disposed substantially centrally thereof. The hole 24 is larger than the diameter of the connector pin but smaller than the outer extension of the hook formations 19. As shown in FIGS. 2 and 3 the pin receiving hollow node 21 is integrally formed with the backing plate 10 and has a hollow space 25 circumscribed by a cone-shaped circumferential sidewall 26. The flat top wall 23 is a circular top wall and the connector pin 16 extends through the hole in substantially concentric spaced alignment therewith and spaced from the peripheral edge 27 of the hole 24. This peripheral edge is sloped inwardly to facilitate assembly or interconnection with the connector pin 16. Because the connector pin is slotted it provides flexible pin segments 16' and by aligning the pins with the hollow nodes 21 the inclined surface 20 of the hook formations 19 will sit on the sloped peripheral edge 27 of the node and by compressing the plates together over the resilient attachment members 12 the pin segments 16' will flex inwardly due to the slope formations being in sliding frictional engagement permitting the pin to enter through the hole 24 into the hollow space 25. Once the pin 16 is entered into the hollow space the pin segments 16' will flex out again providing a captive attachment.

With specific reference now to FIGS. 5 and 6 it can be seen that a helical compression spring 30 is retained in position about the connector pin 16 and the pin receiving node 21 and between the plates to spring bias the plates 10 and 11 apart. At rest, the plates are supported spaced apart by the springs. The spring length is selected that zero or minimum bias holds the hook formations 19 with the flat inner surface 32 of the flat top wall 23 of the node 21. This enables the spring to compress, and the pad to move, as soon as any load is applied to the collector plate. The plates are held apart in substantially parallel planes. The restoring force of the spring and its length are selected to achieve proper sensitivity of the movement detector pad, as is obvious to a person skilled in the art. The hook formations 19 are provided with a flat inner abutment face 31 facing the plate inner surface 17 and extending parallel thereto. These flat abutment faces 31 are disposed for facial contact with the flat inner surface 32 of the flat top wall 23 of the node 21.

Referring again to FIGS. 5 and 6 it can be seen that the collector plate 11 is provided with a circumferential spring locating channel 35 disposed concentrically about the connector pin 16 to receive an end of the helical compression spring 30. A further circumferential spring locating channel 36 is disposed concentrically about the pin receiving hollow node 21 to receive the other end of the helical compression spring 30. The connector pin 16 is of a predetermined length whereby when engaged in its associated hollow node, the plates are maintained spaced apart a predetermined distance with the helical compression spring being retained between the locating channels and under compression to exert a spring force between the plates as above described. A projecting circumferential wall 37 is disposed adjacent the locating channel 35 about the connector pin 16 and outwardly thereof to retain the helical compression spring captive and to facilitate assembly. During assembly the collector plate lies flat on its top surface 11' and the piezoelectric crystal is disposed in its central cavity (not shown). The springs are located within the channels 35 at the base of these projecting circumferential walls 37. The backing plate 10 is simply then disposed over the collector plate in juxtaposition and pressed thereagainst whereby each of the pin 16 will connect with its pin receiving hollow nodes.

The resilient attachment members as above described and illustrated in the drawings have advantages over prior art supports, such as the prior art referred to herein, and maximizes the detection of movement over the entire pad. Current designs provide rigid or semi-rigid corner supports which shunt any movement signal over the corner of the pad directly to the opposite plate of the sensor preventing it from being detected by the piezoelectric compression transducer. With the present invention, movement over the corners of the pad will cause the corner of the pad to deflect and the rigid top plate transfers this movement to the piezoelectric compression transducer which is located at the center of the pad. This flexible corner attachment design also has the ability to hold the collector and backing plates together and provides an easy means of assembly. As can be seen from FIGS. 5 and 6 there is also no rubbing parts, between the outer side wall 16" of the pin 16 and the peripheral edge 27 of the hole 24, which would otherwise cause nagging as the pad moves producing non-linearity in the pad's performance. Because the hole 24 in the hollow nodes 21 is larger in diameter than the pin segments 16' and because the helical compression spring 30 is maintained captive between locating channels, the pin will remain in concentric space position during its up and down movement within the nodes, as is illustrated in FIGS. 5 and 6.

Figure 10:
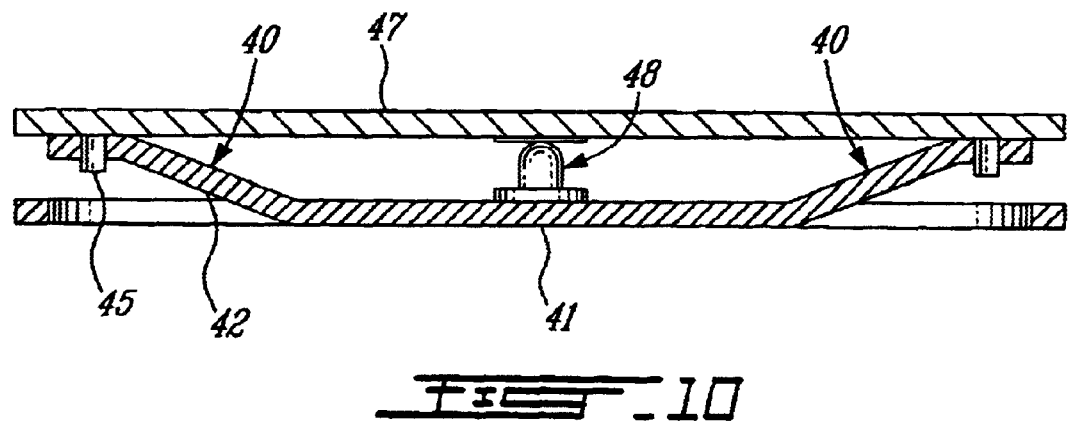
FIG. 10 is a sectional side view of the detector pad of the further embodiment.

Referring now to FIGS. 7 to 10 there will be described a further embodiment of the present invention wherein the resilient attachment members 12 are herein constituted by leaf springs 40. As hereinshown the leaf springs 40 are formed integral with the backing plate 41 which is molded of rigid plastic material. Each of the leaf springs 40 has a straight angulated extension section 42 and a free end connecting section 43. A hole 44 is provided in the free end connecting section 43 whereby to receive therein a peg 45 which is also integrally molded in the inner face 46 of the collector plate 47. The pegs 45 are disposed at predetermined positions whereby when the plates are disposed in facial aligned relationship the pegs 45 will enter into the holes 44 and then be fused thereto. When a load is applied in the corner portions or along the outer edges of the plates there will be flexion which will be detected by the piezoelectric compression transducer 48, as shown in FIG. 10.

It is further pointed out that the backing plate could be made of semi-rigid plastic and that the leaf spring parts profiled to provide the desired separation and spring rate. Furthermore, in order to prevent deterioration of the spring performance due to plastic fatigue; an insert molded metal leaf spring could be molded in the leaf spring section of the plate. Also, the free ends of the leaf springs can be connected to the connector plate by screws extending through the holes instead of using the pegs that are fused over.

It is within the ambit of the present invention to cover any obvious modifications of the preferred embodiment described herein, provided such modifications fall within the scope of the appended claims.

What is claimed is:

1. A movement detector pad comprising a pair of flat plates supported spaced apart in juxtaposed facial alignment and disposed in substantially parallel relationship by resilient attachment members secured between said plates at predetermined positions adjacent an outer circumferential edge of said plates, a piezoelectric compression transducer secured between said plates substantially centrally thereof and generating electric signals when said plates are displaced with respect to one another by displacement of an exterior load positioned above a top one of said plates, said top one of said plates being a collector plate and the other plate being a backing plate; said resilient attachment members spring biasing said plates apart and interconnecting said plates in corner areas thereof, said resilient attachment members each has a connector pin connected to one of said plates and extending transversely to an inner surface of said plate, said connector pin having lateral projecting mean spaced a predetermined distance from said inner surface, and a pin receiving hollow node projecting above an inner surface, of the other of said plates and aligned with said connector pin; said hollow node having a flat top wall with a hole therein for receiving said pin therethrough, a ledge formed about said hole by said top wall, said pin extending into said hole with said lateral projecting means captive thereunder and disposed for facial contact with an inner face of said ledge when biased theragainst, and spring means to spring bias said plates apart with said plates being connected together by said connector pin captive in said node with said lateral projecting means biased against said ledge.

2. A movement detector pad as claimed in claim 1 wherein said spring means is a helical compression spring retained in position about said connector pin and pin receiving node and between said plates.

3. A movement detector pad as claimed in claim 2 wherein said hole is larger than an outer diameter of said connector pin, said helical compression spring being retained captive to maintain said connector pin spaced from a peripheral edge of said hole whereby said pin is displaced in said hole free of friction therewith.

4. A movement detector pad as claimed in claim 3 wherein said hole is a circular hole, said connector pin being a cylindrical slotted pin of plastic material defining opposed pin segments which can flex towards one another, said lateral projecting means being laterally and outwardly extending hook formations integrally formed adjacent a free end of each said pin segments.

5. A movement detector pad as claimed in claim 4 wherein said pin receiving hollow node is integrally formed in said other of said plates, said hollow node having a hollow space circumscribed by a cone-shaped circumferential sidewall, said flat top wall of said node being a circular top wall, said connector pin extending through said hole in substantially concentric spaced alignment therewith and spaced from said peripheral edge of said hole.

6. A movement detector pad as claimed in claim 5 wherein said hook formations have flat inner abutment faces facing said plate inner surface and extending parallel thereto and disposed for facial contact with a flat inner surface of said top wall.

7. A movement detector pad as claimed in claim 3 wherein said one of said plates having said connector pin is provided with a circumferential spring locating channel disposed concentrically about said pin to receive an end of said helical compression spring therein and a further circumferential spring locating channel disposed concentrically about said pin receiving hollow node to receive the other end of said helical compression spring, said pin having a predetermined length whereby when engaged in its associated hollow node said plates are maintained spaced apart a predetermined distance with said helical compression spring being retained between said locating channels and under compression to exert a spring force between said plates.

8. A movement detector pad as claimed in claim 7 wherein there is further provided a projecting circumferential wall adjacent said locating channel about said connector pin and outwardly thereof to retain said coil spring captive.

9. A movement detector pad as claimed in claim 5 wherein said hole in said top wall of said hollow node is provided with an outwardly sloped circumferential edge, said lateral projection of said pin segments having outwardly inclined surfaces for sliding frictional engagement with said sloped circumferential edge to cause said segments to flex towards one another as said pin is forced through said hole in said top wall of said pin receiving hollow node.

10. A movement detector pad as claimed in claim 5 wherein said connector pin is integrally formed with said collector plate, said pin receiving hollow node being integrally formed with said supporting plate.

11. A movement detector pad as claimed in claim 10 wherein said resilient attachment members are provided in each corner of said plates, said plates being square plates having rounded corners.

12. A movement detector pad as claimed in claim 10 wherein said plates are molded from rigid plastic material.

13. A movement detector pad as claimed in claim 1 wherein said resilient attachment members are leaf springs interconnecting corner portions of said pair of plates and holding said plates apart in substantially facially aligned spaced parallel relationship, said leaf springs flexing when a load is applied to a top one of said plates.

14. A movement detector pad as claimed in claim 13 wherein said leaf spring is integrally formed with one of said plates and extends above an inner surface thereof, said leaf springs being attached at a free end thereof to attachment means secured at predetermined locations on an inner face of the other plate in said corner portions.

15. A movement detector pad as claimed in claim 14 wherein said attachment means is a peg dimensioned to engage in a hole provided at said free end of said leaf spring.

16. A movement detector pad as claimed in claim 15 wherein said free end of said leaf springs are disposed in a common parallel plane to said inner face of said collector plate.

17. A movement detector pad comprising a pair of flat plates supported spaced apart in juxtaposed facial alignment and disposed in substantially parallel relationship by resilient attachment members secured between said plates at predetermined positions adjacent an outer circumferential edge of said plates, a piezoelectric compression transducer secured between said plates substantially centrally thereof and generating electric signals when said plates are displaced with respect to one another by displacement of an exterior load positioned above a top one of said plates, said top one of said plates being a collector plate and the other plate being a backing plate; said resilient attachment members spring biasing said plates apart and interconnecting said plates in corner areas thereof, said resilient attachment members being leaf springs interconnecting corner portions of said pair of plates and holding said plates apart in substantially facially aligned spaced parallel relationship, said leaf springs flexing when a load is applied to a top one of said plates, said leaf spring being integrally formed with one of said plates and extending above an inner surface thereof, said leaf springs being attached at a free end thereof to attachment means secured at predetermined locations on an inner face of the other plate in said corner portions.

18. A movement detector pad as claimed in claim 17 wherein said attachment means is a peg dimensioned to engage in a hole provided at said free end of said leaf spring.

19. A movement detector pad as claimed in claim 17 wherein said free end of said leaf springs are disposed in a common parallel plane to said inner face of said collector plate.

* * * * *